United States Patent [19]

Laine et al.

[11] Patent Number: 4,645,837
[45] Date of Patent: Feb. 24, 1987

[54] CATALYST SYSTEM FOR AMINE TRANSALKYLATION

[75] Inventors: Richard M. Laine, Palo Alto, Calif.; Youval Shvo, Tel Aviv, Israel

[73] Assignee: SRI International, Menlo Park, Calif.

[21] Appl. No.: 668,298

[22] Filed: Nov. 5, 1984

Related U.S. Application Data

[63] Continuation-in-part of Ser. No. 288,966, Jul. 31, 1981, abandoned.

[51] Int. Cl.$^4$ ............... C07D 295/12; C07D 295/02; C07C 87/127; C07C 87/20
[52] U.S. Cl. .................................. 544/402; 544/404; 564/470; 564/511; 564/512
[58] Field of Search ............... 544/404, 402; 564/470, 564/511, 512

[56] References Cited

U.S. PATENT DOCUMENTS

| | | | |
|---|---|---|---|
| 3,708,539 | 1/1973 | Fenton | 564/480 |
| 3,726,925 | 4/1973 | Fenton | 564/469 |
| 4,059,640 | 11/1977 | Goetz | 564/391 |
| 4,220,764 | 9/1980 | Imai | 546/246 |
| 4,226,845 | 10/1980 | Laine | 568/451 |
| 4,292,242 | 9/1981 | Laine | |
| 4,430,513 | 2/1984 | Homeier | 564/469 |
| 4,453,019 | 6/1984 | Chang | |
| 4,488,996 | 5/1984 | Yanagi et al. | |
| 4,543,411 | 9/1985 | Knipton et al. | |

FOREIGN PATENT DOCUMENTS

4052018 4/1979 Japan ................ 564/470

OTHER PUBLICATIONS

Bui-the-Khau, et al., ". . . Conversion Primary Amines to Symetrical Tertiary Amines . . . ," J. Org. Chem. 46(8) (1981) pp. 1759-1760.
Bui-the-Khai, et al., ". . . Synthesis of Symetrical Secondary Amines . . . ," J. Organometalic Chem. 208 (1981) 249-251.
Jung, et al., ". . . RuCl$_3$/PR$_3$ Catalyzed Conversion . . . ," Organometallics 2 (No. 8) 1042-4 (1983).
Laine, et al., ". . . Catalytic Exchange of Deuterium for Hydrogen . . . ," J. Am. Chem. Soc. 100, pp. 6527-6528 (1978).
McEwen, et al., "Metallic Palladium . . . ," J. Org. Chem. (1983) 48, 4436-8.
Marahashi, et al., "Palladium Catalyzed Amine Exchanger . . . ," J. Am. Chem. Soc. 100:1 (1978) pp. 348-350.
Shvo et al, "Homogeneous Catalytic Action on C-N Bonds . . . ," J. C. S. (1980) No. 16, pp. 753-754.
Laine, SRI Propos a PYU, 80-059, 2/22/80.
Jachimowicz, F., et al., "Scope of Pathway of Catalytic Aminomethylation . . . ," J. Org. Chem. (1982) 47: 455-447.
Laine, Richard, "Modeling of Heterogeneous Catalyst with Homogeneous Catalysts . . . ," J. Mol. Catalysis, 21 (1983) 119-132.
Murahashi, et al., "Ruthenium Catalyzed Synthesis . . . ," Tetrahedron Let., (23) (1982) pp. 229-232.
Thomson and Laine, "Homogeneous Catalytic Reduction of Benzaldehyde . . . ," pp. 133-145, Abstracts of Papers, Second Chem. Cong., N. America, Aug. 24-29, 1980, Pt. I & II.
Tsuji, et al., "The Platinum Complex Catalyzed Transformation of Primary Amine to Secondary Amine," Chem. Soc. J. Japan.," (1984) pp. 889-890.

Primary Examiner—Glenna M. Hendricks

[57] ABSTRACT

In the transalkylation of tertiary amines, unexpected higher yields are achieved requiring substantially less catalyst and much shorter reaction times at lower reaction temperatures using a homogeneous catalyst in the presence of an alcohol solvent and carbon monoxide. The process may be exemplified by reacting triethylamine and tripropylamine in the presence of a homogeneous triosmiumdodecacarbonyl catalyst, ethanol, and carbon monoxide to prepare diethylpropylamine and ethyldipropylamine.

24 Claims, 4 Drawing Figures

INITIAL RATES/TURNOVER FREQUENCIES FOR RUTHENIUM CATALYZED TRANSALKYLATION AS A FUNCTION OF CO PRESSURE

FIG. 1

INITIAL RATES/TURNOVER FREQUENCIES FOR RUTHENIUM CATALYZED TRANSALKYLATION AS A FUNCTION OF RUTHENIUM CONCENTRATION

FIG. 2

INITIAL RATES/TURNOVER FREQUENCIES AS A FUNCTION OF MOLE PERCENT TRIETHYLAMINE

FIG. 3

INITIAL RATE/TURNOVER FREQUENCY FOR RUTHENIUM CATALYZED TRANSALKYLATION AS A FUNCTION OF F(y)

FIG. 4

CATALYST SYSTEM FOR AMINE TRANSALKYLATION

ORIGIN OF INVENTION

The invention described herein was made in the course of work under U.S. Department of Defense Ofice of Army Research Contract No. DAAG29-81-K-0086 and/or under National Science Foundation Grant Nos. 78-25069 and 82-19541.

REFERENCE TO RELATED APPLICATIONS

This is a continuation-in-part of copending U.S. patent application Ser. No. 288,966 filed July 31, 1981 now abandoned.

TECHNICAL FIELD OF INVENTION

This invention relates to the improvement in the preparation of mixed tertiary amines by the exchange of organic groups between constituents of a mixture of one or more tertiary amines.

BACKGROUND ART

It is known to use Group VIII metal carbonyls as catalysts for water gas shift reactions. See U.S. Pat. Nos. 4,226,845 and 4,453,019 and publications cited therein.

Murahashi, et al., "Catalytic Alkyl Group Exchange Reaction of Primary and Secondary Amines", J. Am. Chem. Soc. July 27, 1983, 105, 5002–5011, teaches the use of palladium catalyst for alkyl group exchange reactions of primary and secondary amines and reported that other metal complexes such as $Ru_3(CO)_{12}$ gave relatively high conversion of the amines, but in low yields.

Fenton, U.S. Pat. No. 3,726,925 describes the preparation of trialkylamine with a metal catalyst, e.g., ruthenium or osmium and the like.

Goetz, U.S. Pat. No. 4,059,640, teaches the reaction of a tertiary amine with alcohol in the presence of carbon monoxide and without metal catalyst.

Both Jung, et al., Organomets. 1983, 2, 1042–1044; and McEwen, et al., J. Org. Chem. 1983, 48, 4436–4438 teach that palladium black is not the catalyst of choice for transalkylation reactions; palladium black loses activity when reacted woth primary, secondary, and/or tertiary amines.

It is believed that the references cited by Youval Shvo and Richard M. Laine in their paper "Homogeneous Catalytic Activation of C—N Bonds. Alkyl Exchange Between Tertiary Amines" (J. Chem. Soc. Chem. Comm., Aug. 1980, pp. 753-754) are the nearest known prior art. Among the references listed by Shvo and Laine is the article of Shun-Ichi Murahashi et al., "Palladium Catalyzed Amine Exchange Reaction of Tertiary Amines. Insertion of Palladium (O) into Carbon-Hydrogen Bonds" (J. of the Am. Chem. Soc., v. 100, Jan. 4, 1978, pp. 348-350). This article discloses an attempt to employ a heterogeneous palladium black catalyst for the exchange reaction of tertiary amines. The exchange reactions described proceed with extreme difficulty, requiring a high reaction temperature and long reaction time. We have conducted similarly the suggested heterogeneous palladium black exchange reaction under milder temperature conditions and have met with little success. In this instance, we found that the reaction time became substantially longer with the accompanying slight decrease in reaction temperature, and the amount of catalyst required was unreasonably high for the poor yield obtained.

Further, heterogeneous catalysts are readily deactivated, or poisoned, by a variety of materials including the amines themselves. This, in turn, requires fairly frequent replenishment or regeneration. In practical terms, this means that such heterogeneous catalytic exchange processes are severely limited in their potential commercial application as a means for reproducing mixed tertiary amines or synthesizing other tertiary amines from tertiary mixtures.

DISCLOSURE OF INVENTION

Objects of Invention

It is therefore an object of the present invention to provide an improved process for the catalytic exchange of organic groups between one or more nitrogen-containing molecular species.

Another object of the present invention is to provide an improved process for the catalytic exchange of organic groups between one or more nitrogen-containing molecular species which results in the novel production of a polymeric mixture.

Still another object of the present invention is to provide an improved process for the catalytic exchange of organic groups between one or more tertiary amine species.

Another object of the present invention is to provide an improved process for the catalytic exchange of organic groups between one or more tertiary amine species which result in the production of a polymeric mixture.

A further object of the present invention is to provide an improved process for the catalytic exchange of organic groups between one or more tertiary amine species, enabling the more efficient production and higher yield of mixed tertiary amines and/or synthesis of tertiary amines.

Other objects and advantages of the present invention will become apparent to those skilled in the art from the accompanying description and disclosure.

STATEMENT OF INVENTION

We have made the surprising discovery that the disadvantages and shortcomings of the prior art process may be overcome by conducting the exchange of organic groups between one or more tertiary amine species employing a homogeneous catalyst in the presence of an alcohol solvent and carbon monoxide. Our process gives unexpected increases in yield while requiring substantially less catalyst, much lower reaction temperatures, and substantially shorter reaction times. In its broadest aspects, the present invention contemplates a process for the exchange of organic groups, involving the breaking of Z—N bonds, between one or more molecular species (i)

where $R^1$ and $R^2$ are the same or different monovalent organic groups bonded to the adjacent nitrogen atom by Z—N bonds or together form a bivalent organic group bonded to the adjacent nitrogen atom by Z—N bonds, Z is carbon or hydrogen, n is zero or a positive integer, $R^3$ is a polyvalent organic group bonded to the adjacent nitrogen atoms by Z—N bonds and is monovalent where n is zero and polyvalent where n is a positive integer, $R^4$ and $R^5$ are the same or different monovalent organic groups bonded to the adjacent nitrogen atom by Z—N bonds or together form a bivalent organic group bonded to the adjacent nitrogen atom by Z—N bonds. The improvement comprises conducting such catalytic exchange reaction employing a homogeneous catalyst in the presence of an alcohol solvent and carbon monoxide, said catalyst being a Group VIII metal complex or salt or mixtures of said metal catalyst.

Examples of suitable R, $R^1$, $R^2$, $R^3$, $R^4$, and $R^5$ organic groups as used hereinabove are methyl, ethyl, propyl, 2-ethylhexyl, octyl, isoctyl, decyl, octadecyl, 3-phenybutyl, cyclobutyl, methylcyclopentyl, cyclohexyl, cyclooctyl, diethylcyclohexyl, phenyl, benzyltoyl, xylyl, duryl, p-amylphenyl, 3,5-dihexylphenyl, etc.

In a more limited aspect, the present invention encompasses a process for the production of mixed tertiary amines by a catalytic exchange of organic groups between a one, two or more component mixture of selected tertiary amines, which process comprises reacting one or more tertiary amines having the general formula (ii) $[-(CH_2)_x NR_2]_k NR_{3-k}$, with one or more selected tertiary amines having the same or different general formulae, (iii) $R_3N$, (iv) $(ZR_3)_j NR_{3-j}$, (v) $[-(CH_2)_x NZR_3]_k NR_{3-k}$, (vi) $NH_2(CH_2)_x NR_2$, (vii) $RNH(CH_2)_x NR_2$, wherein x is from 1 to about 18 carbon atoms; wherein j is 1 to 2; wherein k is 1, 2, or 3; wherein R is the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; wherein $R^6$ is hydrogen or the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; wherein Z is carbon. The improvement comprises conducting such catalytic exchange reaction employing a homogeneous catalyst in the presence of an alcohol solvent and carbon monoxide, said catalyst being a Group VIII metal complex or salt, said metal complex is selected from the group consisting of a complex of cobalt, rhodium, iridium, iron, ruthenium, osmium, and mixtures thereof.

A particular embodiment of the present invention is an improved process for the production of mixed tertiary amines by the catalytic exchange of organic groups between a two or more component mixture of tertiary amines having the same or different general formulae, (iii) $R_3N$ and (iv) $(ZR_3)_j NR_{3-j}$, wherein j is 1 or 2; wherein R is the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; and wherein Z is carbon. The improvement comprises conducting such catalytic exchange reaction employing a homogeneous catalyst in the presence of an alcohol solvent and carbon monoxide, said catalyst being a Group VIII metal complex or salt, wherein said metal complex is selected from the group consisting of a complex of cobalt, rhodium, iridium, iron, ruthenium, osmium, and mixtures thereof.

A specific inventive embodiment of the present invention (hereintofore unknown in the prior art) resides in a process for the preparation of polymeric mixtures having the repeating mer unit (iv)

wherein the (one or more) reacting species is a single tertiary diamine of the above formula (ii) in which n=1.

FIGURES

The invention will be more fully explained with reference to the figures wherein.

MODE(S) FOR CARRYING OUT THE INVENTION

We have unexpectedly found that transalkylation of tertiary amines proceeds most efficiently in alcoholic solvents in the presence of CO, with a transition-metal catalyst. Additional rate enhancement was achieved with the use of a transition mixed-metal catalyst. Other solvents such as THF, Diglme, or Diethylether when employed under CO pressure significantly diminishes transalkylation catalysis rather than enhancing it. Alcohols in the absence of CO promotes rapid catalyst degradation. Moreover, the catalyst will decompose in all solvents in the absence of CO and only maintains its stability under CO pressure. Thus, the effects of alcohol and CO in combination with the transition-metal and/or transition mixed-metal catalysts are clearly unexpected.

The homogeneous catalyst of the invention when used in the presence of alcohol and carbon monoxide is far more active for alkyl exchange than the heterogeneous Pd black catalyst of the prior art. The higher activity has allowed us to reduce the transalkylation reaction temperatures substantially below 200° C. to as low as about 125° C.

The amine reactant of the invention is a tertiary amine. The term tertiary amine is taken to include symmetrical as well as unsymmetrical tertiary amines, tertiary diamines, and higher amines, e.g., tertiary triamines. The reactant tertiary amine species may have one or more of the same or different organic group. Examples of suitable reactant species mixtures include one or more unsymmetrical, one or more unsymmetrical and one symmetrical, two or more symmetrical, one symmetrical and one unsymmetrical, two or more symmetrical and one unsymmetrical, one (tertiary diamine or higher amine) symmetrical, etc.

Examples of some specific tertiary amines and tertiary diamines suitable for use in the process of this invention are:

TERTIARY AMINES trimethylamine, dimethylethylamine, N-methylpyrrolidine, triethylamine, 1,2-dimethylpyrrolidine, 1,3-dimethylpyrrolidine, tri-n-butylamine, 1,2,5-trimethylpyrrolidine, 2-dimethylaminodiethyl ether, dimethyl-aminoacetone, B-dimethylaminoethyl alcohol, B-diethylaminoethyl alcohol, triethanolamine, tropane, 1-diethylamineoisopropyl alcohol, N,N-dimethyl-benzylamine, B,N-dimethyl-otoluidine, 3-diethylaminopropyl alcohol, methyl-2-pyridyl ketone, diethylaminopropylamine, N,N-dimethyl-2,6-dimethylaniline, N-methyl-N-ethylaniline,N,N-dimethyl-2,5-dimethyl-aniline, N,N-dimethyl-2,4-dimethylaniline, N,N-diethyl-2-methylaniline, N,N-dimethyl-2-chloroaniline, N,N-dimethyl-4-methylaniline, tri-n-butyl-amine, N,N-dimethyl-3-methylaniline, N,N-diethylaniline, N,N-diethyl-4-methylaniline, 2-dimethylaminobenzaldehyle, tri-isoamylamine, N,N-dipropylaniline, tri-n-amylamine, 3-bromo-N,N-dimethylaniline, N-benzyl-N-methylaniline, 2-nitro-N,N-dimethylaniline, 2,2'bis(-dimethyl-amino)-biphenyl, N,N-dimethyl-4-aminophenol, 4-nitroso-N,N-dimethyl-aniline, 4,4'-bis-(dimethylamino)-diphenylmethane, tribenzylamine, N-methyl-Y-pyridone, 4-dimethylaminoazobenzene quinuclidine, hexamethylene tetramine and etc.

TERTIARY DIAMINES tetramethylhexanediamine, tetramethylmethanediamine, N,N-diethyl-1,-3-propanediamine, tetraethylethylenediamine, ethyltripropylethylene-diamine, tetraethylethylenediamine, triethylpropylethylenediamine, tetra-n-propylethylenediamine, N,N-diethylethylenediamine, N,N-diethyl,N',N'-dipropylethylenediamine, N,N'N'dimethylethylenediamine, N,N,N',N'tramethylethylenediamine, N,N,N'N'tetramethylpropylenediamine, N,N'dipropyl,N,N'diethylethylenediamine, N,N'diethanol,-N'N'dimethylethylenediamine, N,N,N'triethanol-N'methylethylenediamine, N,N,N'N'-tetramethyl-1,3-butanediamine, N,N,N'N'-tetramethylethylenediamine, N methyl N ethanol, N'N'dimethylethylenediamine, N,N,N'N'-tetramethyl-1,3-butanediamine, N,N,N'N'-tetramethylethylenediamine, N,N,N',N'-tetrakis-(2-hydroxypropyl)-ethylenediamine, N,N trimethylsilylethyl, N',N'diethylethylenediamine, etc.

It is understood that the aforementioned tertiary amines and tertiary diamines are only representative of the class of tertiary amines which may be employed as reactant materials of the process of the present invention and that the invention is not necessarily limited thereto.

Inasmuch as the above examples of tertiary amines are useful as starting materials, they may be considered as specific examples of the types of tertiary amines and tertiary diamines which may be prepared according to the process of this invention. Moreover, any tertiary amine or tertiary diamine produced by the process of the present invention can also be considered as suitable starting materials or intermediates for synthesis of other tertiary amines, tertiary diamines, or other resultant products by the process of the present invention.

The homogeneous catalyst of this invention is a catalyst comprising a Group VIII metal complex or salt. The inert alcohol solvents employed insure a substantially all homogeneous reaction solution; they are necessary to the successful performance of the exchange reaction. Optionally, modifying ligands may also be added to the solution for further stability. Group VIII metals and mixed metals selected for their demonstrated activity include cobalt, iridium, osmium, rhodium, ruthenium, iron-cobalt, iron-iridium, iron-osmium, iron-rhodium, and iron-ruthenium, the preferred metals being iridium, osmium, ruthenium and their mixtures with iron. The more preferred metals are ruthenium, iridium, osmium, and their mixtures with iron. The most preferred metals are ruthenium and iron-ruthenium.

Some examples of chelating agents and anions suitable for forming complexes and salts with the Group VIII metals include ammonia, carbon monoxide, carboxylic acids, 1,3-diketones, e.g., acetylacetone, proprionylacetone, benzoylacetone, and the like; aminoalcohols, e.g., triethanolimine, N-hydroxyethylethylenediamine, and the like; and ligands of phosphorus, arsenic and antimony, e.g., triphenylphosphines, triphenylphosphites, triphenylarsines, triphenylarsenites, and the like.

The carbonyl complexes of the Group VIII metals are especially suitable for use in the present process. The carbonyl of the Group VIII metal may be purchased as separate metal carbonyls and, if desired, mixed in any proportions for use as a catalyst mixture. The metal carbonyl complex may also be prepared in situ from any salts or oxides of the metals during the course of the exchange reaction. The metals may be in any valence state inasmuch as the carbon monoxide reduces the metal ions to their lowest valence state.

Some specific examples of suitable homogeneous catalysts that can be employed in the process of this invention include cyclopentadienyl-cobaltdicarbonyl dimer, dicobaltoctacarbonyl, triphenylphosphinecobalt-tricarbonyl dimer, hydridocarbonyltris(triphenylphosphine)iridium, iodocacarbonylbis(triphenylphosphine)iridium, cyclopentadienylirondi-carbonyl dimer, iron nonacarbonyl, iron pentacarbonyl, hydridocar-bonyltris-(triphenylphospine)rhodium, rhodium acetate, tetrarhodium dodecacarbonyl, ruthenium acetaylacetonate, etc.

Specific examples of more preferred metal carbonyls and their mixtures include: $Ir_4(CO)_{12}$, $Os_3(CO)_{12}$, $Rh_6(CO)_{16}$, $Ru_3(CO)_{12}$, $Fe_3(CO)_{12}/Ir_4(CO)_{12}$, $Fe_3(CO)_{12}/Os_3(CO)_{12}$, $Fe_3(CO)_{12}/Rh_6(CO)_{16}$, $Fe_3(CO)_{12}/Ru_3(CO)_{12}$, $Os_3(CO)_{12}/Rh_6(CO)_{16}$, $Ru_3(CO)_{12}/Ir_4(CO)12$, $Ru_3(CO)_{12}/Fe(CO)_5$, $Ir_4(CO)_{12}/Fe(CO)_5$, $Os_3(CO)_{12}/Fe(CO)_5$, $Rh_6(CO)_{16}/Fe(CO)_5$, $Ir_4(CO)_{12}/Fe_3(CO)_{12}$, $Os_3(CO)_{12}/Fe_3(CO)_{12}$, $Rh_6(CO)_{16}/Fe_3(CO)_{12}$, $Ru_3(CO)_{12}/Fe_3(CO)_{12}$, $H_2Os_3(CO)_{16}$, $H_4Ru_4(CO)_{12}$, $H_8Ru_2Fe_2(CO)_{12}$, $NaHRu_3(CO)_{11}$m $Na_2Fe(CO)_4/Ru_3(CO)_{12}$, and etc.

The catalyst may be employed in amounts of 25 mmole or less to 150 mmole or more percent based upon the tertiary amine or diamine starting material.

Suitable alcohol solvents for use in the process of the present invention are e.g., ethanol, methanol, isopropanol, butanol, isobutanol, pentanol, hexanol, isohexanol, heptanol, isooctanol, nonanol, decanol, phenol, cresol, xylenol, cumenol, isocumenol, ethoxyethanol, tetradecanol, decanol, dodecanol, hexadecanol, octadecanol, eicosanol, cyclohexanol, methylcyclopentanol, ethylcyclohexanol, cyclononanol, 3-cyclohexyloctanol, 3-cyclohexyl-4-methyldodecanol, 2-phenylethanol, 3-phenyloctanol, 4-totyl-6-metnyldodecanol, and the like. Examples of preferred alcohols are methanol, ethanol, propanol, tetrahydrofaranol, n-butanol, and isoproponol.

With respect to the amount of alcohol that may be employed in the present invention with positive and beneficial effects, it is found that as little as about 10 wt % is effective to cause the reaction to proceed, while amounts up to about 98 wt % or more may be employed to advantage.

The reaction is preferably carried out at a temperature of about 100° to about 180° C., more preferably about 125° C. to about 160° C., and most preferably between about 125° C. to about 150° C.

Carbon monoxide may be employed at pressures of 10 psi or less to about 200 psi or more. Optionally, other gases such as $N_2$, Ar, and the like may be added along with CO.

Examples of suitable modifying ligands for use in the process of this invention include: trimethylphospine, trimethylphosphite, triethylarsine, trisopropylstibine, tributylarsine, triamylphosphine, ethyldiisopropylstibine, tricyclohexylphosphine, tricyclohexylstibine, triphenylphosphine, triphenylphosphite, tris(o-tolyl)phosphine, tris(2-ethylhexyl)arsine, tris(methylcyclopentyl)stibine, phenyldiisopropylphosphine, phenyldiamylphosphine, ethyldiphenylphosphine, methyldixylylphosphine, isopropyldiphenylphosphite, tritolylphosphine, tricyclohexylphosphite, tri(methylcyclopentyl)arsine, tritolylstibine, tris(3,5-diethylphenyl)phosphine, tricumylarsine, etc.

To demonstrate the unexpected effect of homogeneous catalyst-alcohol-carbon monoxide on transalkylation of tertiary amines, a number of studies were performed under various conditions, as indicated below.

All secondary and tertiary amines were purchased from Aldrich and distilled from $CaH_2$ under Ar or $N_2$ prior to use. Ethanol was purified in the same manner. Methanol was purified via distillation from $Mg(OMe)_2$ under Ar, THF, diglyme, ethyl ether, and n-butyl ether were purified by distillation from sodium benzophenone ketyl under $N_2$ and stored under $N_2$ prior to use. Catalyst precursors were purchased from Strem Chemicals and used as received. $Ru_3(CO)_{12}$ and $Fe_3(CO)_{12}$ were stored in a Dri-Box under $N_2$.

Product analyses were performed on a Hewlett Packard 5880A reporting GC equipped with FID using a 2.5 m × 0.325 cm column packed with 60/80 carbowax/4% carbowax 20M/0.8% KOH on acid washed chromsorb W (supplied by Supelco). N-butyl ether was used as an internal standard for GC analyses. Infrared spectra were obtained using a Perkin-Elmer 281 IR spectrophotometer. NMR spectra were taken on a JEOL 90-MHz instrument. GC-Mass Spectral analyses were performed using an LKB-9000 mass spectrometer or a Ribermag R 10 10 C.

Stock solutions of amines were prepared, in appropriate solvents, with n-butyl ether as an internal standard. The solutions, normally 0.67M in both $Et_3N$ and $Pr_3N$ unless indicated otherwise, were stored under Ar at 0° C. and analyzed prior to use. Magnetically stirred, 34 ml quartz-lined bomb reactors were dried by heating at 120° C., then cooled and stored in a desiccator until used.

A. In a typical reaction, the required quantity of $Ru_3(CO)_{12}$, usually 0.05 mmol (32 mg) or as noted, was weighed under $N_2$ and transferred to a bomb reactor. The reactor was then loaded with 5 ml of stock solution. The reactor was sealed and degassed via three pressurization/depressurization cycles using 500 psig of $N_2$ or CO and then pressurized to the desired pressure with $N_2$ or CO (normally 100 psig) and heated in an oil bath to 160°±0.5° C. Samples were taken at appropriate times (usually 15 min) by cooling the reactor in an ice bath, depressurizing and removing a 0.1 ml sample. The reaction was then restarted following the above procedure.

B. A second set of reactions was conducted as in A but with slight modifications. In these reactions, the solvent used was either ethanol, THF or diglyme. The reaction conditions were as follows. In the standard reactor were mixed 5 ml of dry solvent containing 1 mmol of n-butyl ether as an internal standard, 0.05 mmol of $Ru_3(CO)_{12}$, and 2.0 ml of a 1:1 molar ratio (6.0 mmol:6.0 mmol) of $Et_3N$ and $Pr_3N$. When the reactions were studied under CO, the reactor was degassed with CO and pressurized to 100 psig CO. Otherwise the same procedure was followed with $N_2$. The reactions were sampled every 0.5 h for the first 2 h and every hour thereafter until the mole percentage of mixed alkyl amines approached 70% or until the mole percentage of mixed alkyl amines failed to change significantly indicating catalyst degradation.

Figure 1:
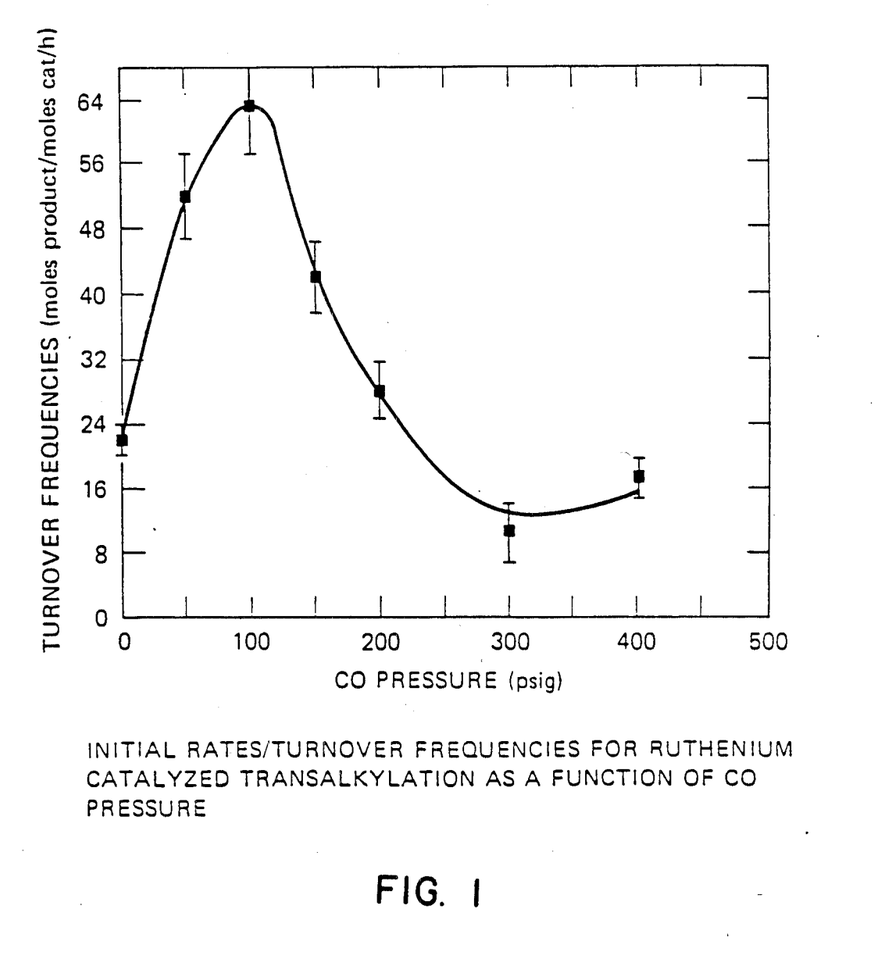
FIG. 1. graphically illustrates the effect of CO pressure on turnover frequency (TF=moles deuterated amine produced/mol of $Ru_3(CO)_{12}$—hour per hour) for reactions in methanol under 100 psig CO at 160° C. at a total constant volume of 5.0 mL and $[Et_3N]=[Pr_3N]=0.74M$ showing an initial reaction rate enhancement as the CO pressure increases to approximately 100 psig followed by a rapid decline in catalyst activity with increased CO pressure.

Carbon Monoxide: Reactions were run as described in procedure A with $Et_3N$ and $Pr_3N$ amine concentrations of 0.74M and using methanol as the only solvent. The CO pressure was varied from 0 to 400 psig at ambient temperature. As shown in FIG. 1, there is an initial rate enhancement as the CO pressure increases to approximately 100 psig. Any further increases in CO pressure cause a rapid decline in catalyst activity.

Figure 2:
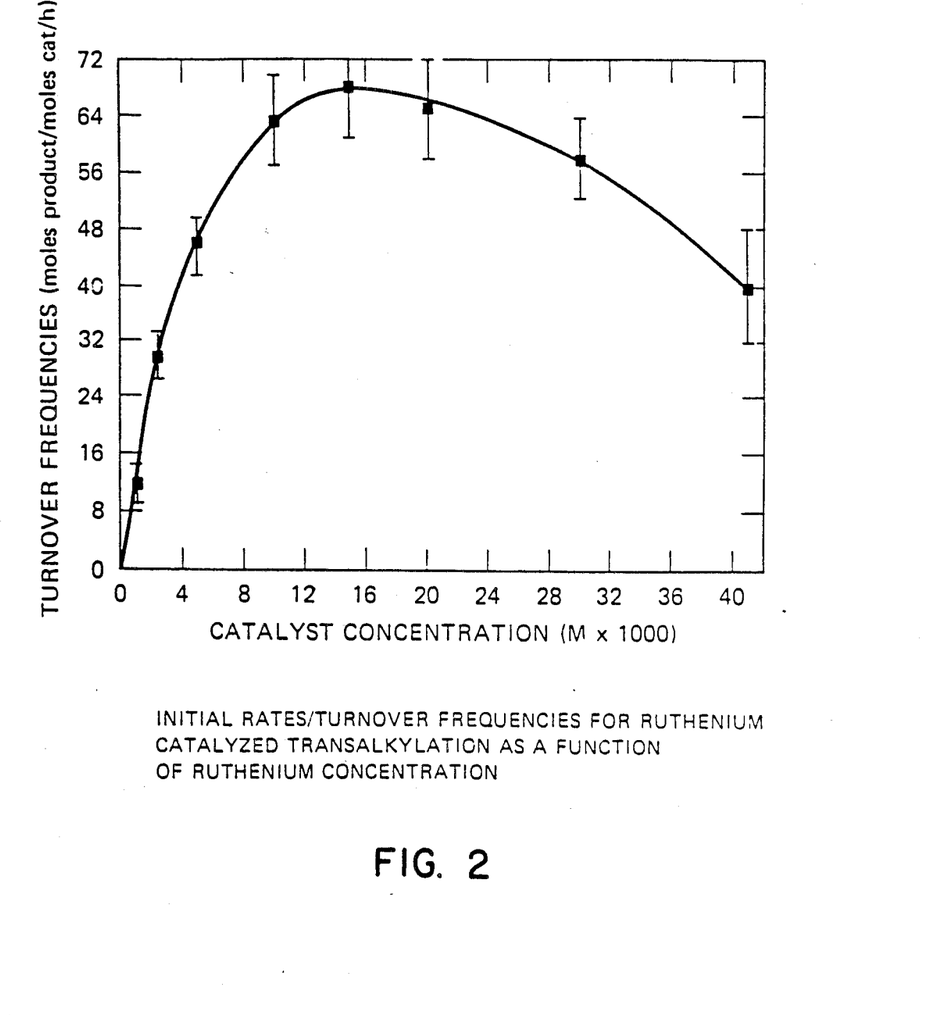
FIG. 2. graphically illustrates the effect of catalyst concentration on turnover frequency (TF=no. of moles of $Et_2NPr$ produced/mole of $Ru_3(CO)_{12}$—hour) for reactions in methanol under 100 psig Co, at 160° C. at a total constant volume of 5.0 mL and $[Et_3N]=[Pr_3N]=0.74M$ showing rapid increase in product yield with increase catalyst concentration and a gradual decline above the 75 mmol level.

Catalyst Concentration: Reactions were run as described for procedure A in the general procedures. Reactions were conducted in methanol under 100 psig of CO at 160° C. The solutions were 0.87M in total amine concentration with a 1:1 ratio of $Et_3N$ to $Pr_3N$. $Ru_3(CO)_{12}$ concentrations were varied between $5.0 \times 10^{-3}M$ and $4.0 \times 10^{-2}M$. The results shown in FIG. 2 indicate that the product yield is not linearly dependent on catalyst concentration, indicative of cluster-catalyzed reactions.

Figure 3:
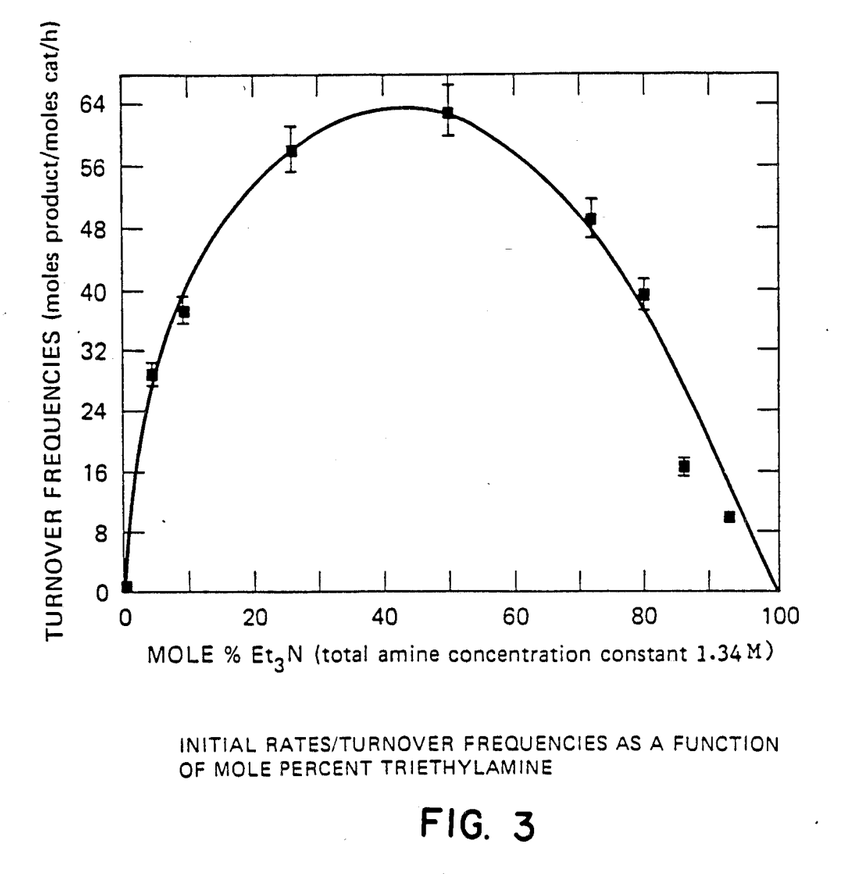
FIG. 3. graphically illustrates the effect of turnover frequencies as a function of mole percent triethylamine (TF=no. of moles of $Et_2NPr$ produced/mole of $Ru_3(CO)_{12}$—hour) for reactions in methanol with 0.05 mmol $Ru_3(CO)_{12}$, under 100 psig CO, at 160° C. at a total constant volume of 5.0 mL and a total constant amine concentration of 1.34M.

Amine Concentration: Reactions were run as in the CO pressure reactions with the exception that the CO pressure was held constant at 100 psig CO. The overall amine concentration was varied from 0.2M to 3.7M. The ratio of $Et_3N$ to $Pr_3N$ was maintained at 1:1 (FIG. 3). Reactions were then conducted in which the ratio of $Et_3N$ to $Pr_3N$ was varied with the total amine concentration held constant at 1.34M (FIG. 3a).

By way of comparison, Table I illustrates the advantages of the use of alcohol solvents and carbon monoxide employing the homogeneous catalyst system of the invention.

TABLE 1
Initial Rates and Final Mole Percentages for Transalkylation in Various Solvents

| Solvent[a] | Initial Rates[b] | | Final mol % Mixed-Alkyl Amines | Final Time (h) |
|---|---|---|---|---|
| | $N_2{}^c$ | 100 psi CO | | |
| THF | 80 | 2.4 | 48 | 3 |
| Diglme | 45 | 4.3 | 40 | 7 |
| Diethylether | 19 | 7 | 47 | 4 |
| Methanol | 22 | 63 (160°) | 63,70 | 4 |
| | | 13 (145°) | | 16 |
| | | 5.6 (130°) | | |
| Ethanol | 18 | 28 | 61 | 16 |
| | | 46[d] | 64[d] | 4.5 |

[a]Reactions were run as in procedure A of experimental for diethyl ether and methanol and as in procedure B for THF, diglime, and ethanol. Reaction solutions in diethy ether and methanol were *0.67 M in each amine and 0.67 M for the other solvents.
[b]Initial rates are defined as turnover frequency (TF), where TF is defined as moles of $Et_2NPr$/moles of catalyst precursor-hour.
[c]In the absence of CO pressure, the catalyst will decompose in all solvents. Evidence of catalyst decomposition is usually visible after one hour.
[d]In mixed-metal catalyst systems, 0.15 mmol of $Fe(CO)_5$ was added to the standard reaction.

Figure 4:
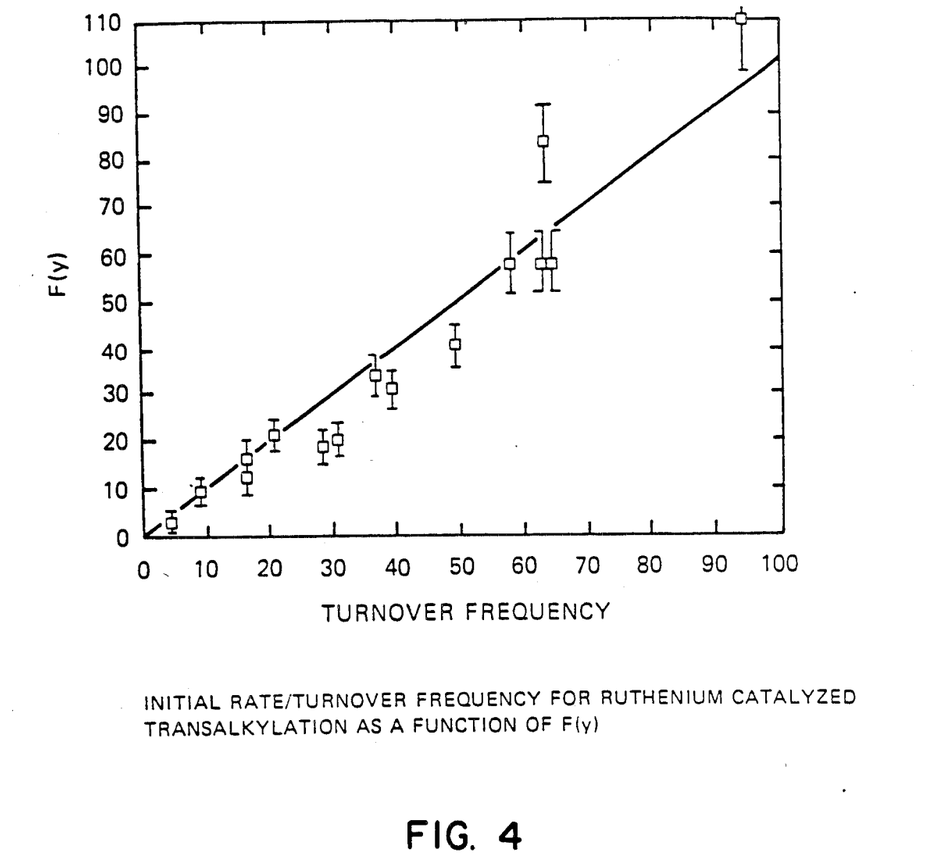
FIG. 4. graphically illustrates the effect of initial rate/turnover frequency for ruthenium catalyzed transalkylation as a function of F(y) where $F(y)=(k_1 k_2 [E+_3N][Pr_3N])/(k_{-1}+k_2[Pr_3N])+(k_3 k_4[E+_3N][Pr_3N])/(k_{-3}+k_4[E+_3N])$ where $k_1=125$; $k_{-1}+273$; $k_2=547$; $k_3=40$; $k_{-3}=250$; and $k_4=202$

In a second set of studies, initial rates were measured as a function of changes in the total amine concentration keeping the ratio of $Et_3N:Pr_3N$ constant at 1:1. The results of both studies were used to develop by multivariant analysis the transalkylation rate expression $F(y)=d[Et_2NPr]/dt$ of FIG. 4 above. The line drawn through the data points of FIG. 4 is the rate predicted from $F(y)$ using the optimized values for $k_1-k_4$.

Temperature Studies: Reaction rate data were obtained for the reaction:

run in methanol at several temperatures as recorded in Table I. These data allow us to calculate the energy of activation, $Ea=24\pm1$ kcal/mol.

Other Products: In addition to the transalkylation reaction, we observe another reaction that consumes $Et_3N$ irreversibly. The remarkable reaction:

proceeds very slowly under the conditions employed in the studies, except at high catalyst concentration.

INDUSTRIAL APPLICABILITY

Tertiary amines made by the process of this invention are useful as emulsifiers, corrosion inhibitors, lubricating oil and fuel additives, biocides, fungicides, surfactants, curing agents, catalysts, plasticizers, soil conditioners, detergents, intermediates in the manufacture of dyes, explosives, phase-transfer catalysts, polymerization catalysts, and pharmaceuticals. For example, tributylamine is used as a solvent, as an intermediate in the preparation of other chemicals and as an inhibitor in hydraulic fluids; triallylamine is used in the preparation of quaternary ammonium salts which copolymerize to form cross-linked polymers, and benzyldimethylamine is used to produce quaternary ammonium compounds, as a methylating agent in organic syntheses, as a catalyst, and as an ingredient in epoxy resins. The process of this invention is useful for selectively synthesizing tertiary amines and tailoring mixed tertiary amine combinations. For example, the process of the invention also can be used for the preparation of quaternary amine polymers, amine macrocycles, including analogs of crown ethers, cryptands, and cryptates.

The invention is further illustrated by means of the following illustrative embodiments, which are given for purpose of illustration only and are not meant to limit the invention to the particular reactants and amounts disclosed.

The reaction as described in the examples below is carried out in batch fashion in a bomb but continuous procedures may be employed.

The following examples illustrate the invention and demonstrates the results actually obtained.

EXAMPLE 1

N,N,N',N'tetramethylethylene diamine

In a magnetically stirred 34 ml quartz-lined bomb reactor, were mixed 5 ml of dry ethanol containing 1 mmol of n-butyl ether as internal standard for GC analyses, 64 mg (0.1 mmol) of $Ru_3(CO)_{12}$, 44 ul of $Fe(CO)_5$ (0.3 mmol) and 2.0 ml (13.2 mmol) of N,N,N',N'tetramethylethylene diamine. The reactor was sealed and degassed via three pressurization/depressurization cycles with 500 psig of CO and then pressurized to 100 psig with CO and heated to 160° C. for 2 h. At the end of this period, the reactor is cooled, depressurized and analyzed by GC. The GC analysis showed small amounts of $Me_3N$. After 120 h of reaction, approximately 7 mmol of $Me_3N$ are formed along with 3 mmol of N,N'-dimethylpiperazine, 0.5 mmol of N-ethyl, N,N',N'trimethylethylene diamine, 0.5 mmol of N,N,N',N'',N''pentamethyldiethylene triamine [$Me_2NCH_2CH_2N(Me)CH_2CH_2NMe_2$] and 1.5 mmol of N-methyl, N'-(2-dimethylaminoethyl)piperazine.

EXAMPLE 2

N,N,N',N'tetraethylethylene diamine

The same procedure as used for the tetramethyl derivative is used for tetraethylethylene diamine (2.0 ml=9.4 mmol). After 16 h of reaction time, GC analysis showed production of 2.5 mmol of $Et_3N$. After an additional 84 h reaction time, a total of 4.2 mmol of $Et_3N$ was produced along with four other major products including 1.7 mmol of N,N,N',N''',N''pentaethyldiethylene triamine, [$Et_2NCH_2CH_2N(Et)-CH_2CH_2NEt_2$], 0.8 mmol of N,N,N'',N''',N'''',N''''heptaethyltriethylene tetramine, $Et_2N-[CH_2CH_2N(Et)]_2-CH_2CH_2NEt_2$, 0.1 mmol of the per-ethyltetraethylene pentaamine, traces of the pentaethylene hexamine, traces of the N,N'diethylpiperazine and the N,N',N''triethyl-1,4,7-triazacyclononane. We also observed the formation of 0.1 mmol of N,n-butyl, N,N',N'triethylethylenediamine.

EXAMPLE 3

N,N,N',N'tetramethylhexamethylene diamine

The same procedure as used for the tetramethylethylene diamine derivative is used for tetramethylhexamethylene diamine (2.0 ml=9.4 mmol). After 16 h reaction time, GC analysis showed production of small amounts of $Me_3N$. After an additional 96 h of reaction time, GC-Mass spectral analysis reveals that 25% of the amine reacted to give, very selectively, 2.1 mmol of the open chain dimer, N,N,N',N'',N''-pentamethyl-1,7,15-triazapentadecane and a trace (0.2 mmol) of the N-ethyl, N,N',N'trimethylethylene diamine.

The following specific examples will serve further to illustrate the practice and advantages of the invention.

EXAMPLE 4

In a quartz-lined Parr general purpose bomb reactor is added 14 mmoles of triethylamine, 14 mmoles of tripropylamine, 5 ml of methanol alcohol and 0.05 mmol of $Ir_4(C))_{12}$ under 100 lb $in^{-2}$ CO at 125° C. for 3 hours. The contents are removed and analyzed. This procedure is employed in each of the examples set forth in Table II. The numerical values correspond to (mol mixed amine)/(total mol amine)×100 and are reproducible to ±5% of the indicated value.

TABLE II

| Catalyst Complex | Mole % of mixed amines | |
|---|---|---|
| | Conversion to diethylpropylamine | Conversion to ethyldipropylamine |
| $Rh_6(CO)_{16}$ | 5% | 5% |
| $Ir_4(CO)_{12}$ | 35% | 35% |
| $Ru_3(CO)_{12}$ | 60% | 60% |
| $Os_3(CO)_{12}$ | 59% | 59% |

EXAMPLE 5

In a quartz-lined Parr general purpose bomb reactor is added 14 mmoles of triethylamine, 14 mmoles of tripropylamine, 5 ml of n-butanol alcohol, and 0.05 mmol of $Os_3(C))_{12}$ catalyst under 10 lb $in^{-2}$ CO at 150° C. for 3 hours. The contents are removed and analyzed. This procedure is employed in each of the examples set forth in Table III. The numerical values correspond to (moles mixed amine)/(total moles amine)×100 and are reproducible to ±5% of the indicated value.

TABLE III

| Catalyst Complex | Mole % of mixed amines | |
|---|---|---|
| | Conversion to diethylpropylamine | Conversion to ethyldipropylamine |
| $Rh_6(CO)_{16}$ | 3% | 3% |
| $Ir_4(CO)_{12}$ | 30% | 30% |
| $Ru_3(CO)_{12}$ | 40% | 40% |
| $Os_3(CO)_{12}$ | 35% | 35% |

EXAMPLE 6

The following example illustrates the shortcomings and disadvantages of the prior art heterogeneous palladium black catalyst and demonstrates the results actually obtained:

In a quartz-lined Parr general purpose bomb reactor was added 14 mmol of triethylamine, 14 mmol of tripropylamine, 0.1 m of $H_2O$, and 0.75 mmol catalyst under 100 lb $in^{-1}$ $N_2$ at 150° C. for 20 hours. The contents were removed and analyzed. The result is set forth in Table IV.

TABLE IV

| Catalyst | Mole % of mixed amine | |
|---|---|---|
| | Conversion to diethylpropylamine | Conversion to ethyldipropylamine |
| Pd black | 1.6 | 1.6 |

The following examples illustrate other modes of practice of the present invention.

EXAMPLE 7

In a quartz-line Parr general purpose bomb reactor is added 5.17 grams of tetraethylethylenediamine, 5.0 ml of methanol alcohol, and 64 mg (0./1 mmol) of $Ru_3(CO)_{12}$ under 80 lb $in^{-1}$ CO at 150° C. for 39 hours. The contents are removed and analyzed by GC Mass Spectroscopy which indicated (allowing for sensitivity differences) 20% triethylamine, 5% N,N'diethylpiperazine, 12% pentaethyldiethylenetriamine, and the remainder to be derivatives of triethylenetetramine and tetraethylenepentamine.

EXAMPLE 8

In a quartz-line Parr general purpose bomb reactor are added 20 mmoles of trimethylamine, 20 mmoles of tri(n-butyl)amine, 4 ml of isopropyl alchol, and 0.04 mmol in 1:1 ratio of $Ru_3(CO)_{12}/Fe_3(CO)_{12}$ catalyst under 90 lb $in^{-2}$ CO at 150° C. for 3 hours. The contents are removed and the products dimethyl(n-butyl)amine and di(n-butyl)methylamine recovered therefrom.

In a quartz-lined Parr general purpose bomb reactor are added 20 mmoles of N-methylpiperidine, 20 mmoles of tri-n-propylamine, 4 ml of butanol, and 0.1 mmol in 1:1 ratio of $Os_3(CO)_{12}/Fe_3(CO)_{12}$ catalyst under 10 lb $in^{-2}$ CO at 150° C. for 3 hours. The contents are removed and the products dipropylmethylamine and N-propylpiperidine recovered therefrom.

In a quartz-lined Parr general purpose bomb reactor are added 20 mmoles of (tri-iso-butyl)amine, 20 mmoles of tri-n-octylamine, 5 mL of isobutyl alcohol, and 0.1 mmol in 1:1 ratio of $Ir_4(CO)_{12}/Fe_3(CO)_{12}$ catalyst under 50 lb $in^{-2}$ CO at 150° C. for 3 hours. The contents are removed and the products isobutyldi-n-octylamine and diisobutyl-n-octylamine recovered therefrom.

In a quartz-lined Parr general purpose bomb reactor are added 20 mmol of dimethylbenzylamine, 5 ml of methyl alcohol, and 0.1 mmoles in 1:1 ratio of $Rh_6(CO)_{16}/Fe_3(CO)_{12}$ catalyst under 100 lb $in^{-2}$ CO at 150° C. for 3 hours. The contents are removed and the products trimethylamine, tribenzylamine and methyldibenzylamine recovered therefrom.

In a quartz-lined Parr general purpose bomb reactor are added 20 mmoles of trimethylamine, 20 mmoles of tribenzylamine, 5 ml of methyl alcohol, and 0.4 mmol in 1:1 ratio of $Ir_4(CO)_{12}/Ru_3(CO)_{12}$ catalyst under 100 lb $in^{-2}$ CO at 150° C. for 3 hours. The contents are removed and the products dibenzylmethylamine and dimethylbenzylamine recovered therefrom.

In a quartz-lined Parr geneal urpose bomb reactor are added 20 mmoles of (trimethylsilylmethyldiethylamine, 20 mmol of tripropylamine, 0.1 ml of methyl alcohol, and 0.4 mmol in 1:1 ratio of $Ru_3(CO)_{12}/Os_3(CO)_{12}$ catalyst under 10 lb $in^{-2}$ CO at 150° C. for 4 hours. The contents are removed and the products (trimethylsilylmethyl)ethylpropylamine, dipropylethylamine, propyldiethylamine, triethylamine and (trimethylsilylmethyl)-dipropylamine recovered therefrom.

In a quartz-lined Parr general purpose bomb reactor are added 20 mmoles of (trimethylsilylmethyl)dibenzylamine, 20 mmoles of trimethylamine, 5 ml of butyl alcohol and 0.5 mmol of $Os_3(CO)_{12}$ catalyst under 9 lb in$^{-2}$ CO at 150° C. for 4 hours. The contents are removed and the products (trimethylsilylmethyl)-methylbenzylamine, benzyldimethylamine, dibenzylmethylamine, tribenzylamine, and (trimethylsilylmethyl)dimethylamine recovered therefrom.

In a quartz-lined Parr general purpose bomb reactor are added 20 mmoles of N-isopropylpiperidine, 20 mmol of (triphenylsilylethyl)diethylamine, 5 ml of methyl alcohol, and 0.05 mmoles of $Ru_3(CO)_{12}$ catalyst under 60 lb in$^{-2}$ CO at 150° C. for 4 hours. The contents are removed and the products (triphenylsilylethyl)ethylisopropylamine and n-ethyl-piperidine recovered therefrom.

EXAMPLE 9

In a quartz-lined Parr general purpose bomb reactor are added 10 grams of dimethyl-2-ethoxyethylamine, 5 ml of ethyl alcohol, 0.05 mmol in 1:1 ratio of $Os_3(CO)_{12}/Ir_4(CO)_{12}$ catalyst under 15 lb in$^{-2}$ CO at 150° C. for 10 hours. The products are trimethylamine, di-2-ethoxyethylmethylamine and tri-2-ethoxytethylamine, recovered therefrom.

In a quartz-lined Parr general purpose bomb reactor are added 5 grams of N,N,N',N'tetramethylpropylenediamine, 5 grams of N,N-diethyl-ethylenediamine, 5 ml of methyl alcohol, 0.05 mmoles of $Os_3(CO)_{12}$ catalyst under 5 lb in$^{-2}$ CO at 150° C. for 10 hours. The contents are removed and the products dimethylamine, methylamine, ammonia, N,N-dimethyl,N''N''diethylethylenepropylenetriamine, N,N-dimethyl,N'''-ethylethylenepropylenetriamine, N,N-dimethyl-N'-methylethylenepropylenetriamine, N,N'diethyl-N,N'ethylmethyl-N,N'dimethyl-piperazine and higher oligomers recovered therefrom.

In a quartz-lined Parr general purpose bomb reactor are 10 grams of N,N'-dimethylethylenediamine, 5 ml of ethyl alcohol, 0.05 mmoles in 1:1 ratio of $Os_3(CO)_{12}/Fe_3(CO)_{12}$ catalyst under 40 lb in$^{-2}$ CO at 150° C. for 10 hours. The contents are removed and the products ammonia, dimethylamine, trimethylamine, N,N-dimethyl, N'',N''dimethyldiethylenetriamine, N,N dimethyl-N'methyl diethylenetriamine, N'methyl-diethylenetriamine, N,N'dimethylpiperazine and higher oligomers recovered therefrom.

In a quartz-lined Parr general purose bomb reactor are added 5 grams of N,methyl,N'N'dimethylethylenediamine, 5 grams of tetraethylethylenediamine, 5 ml of methyl alcohol, 0.05 mmol of $H_2Os_3(CO)_{10}$ catalyst under 0.1 lb in$^{-2}$ CO at 150° C. for 10 hours. The contents are removed and the products dimethylamine trimethylamine, ethylmethylamine diethylmethylamine, dimethylethylamine, N,N,N'',N''tetramethyldiethylenetriamine, N-methyl, N'-methyl,N''N''diethyldiethylenetriamine, N-methyl,N'-methyl,N'',N''diethyldiethylenetraimine, N-methyl,N'ethyl,N''N''diethylethylenetriamine, N,N-dimethyl,N'ethyl,N',N''diethyldiethylenetriamine, and N,N-dimethyl,N'',N''diethyldiethylenetriamine recovered therefrom.

In a quartz-lined Parr general purpose bomb reactor are added 5 grams of triethanolamine, 5 grams of tetramethylethylenediamine, 5 ml of butyl alcohol, 0.07 mmol of $Ru_3(CO)_{12}/Ir_4(CO)_{12}$ catalyst under 50 lb in$^{-2}$ CO at 150° C. for 10 hours. The contents are removed and the products N'methyl-N-ethanol, N'N'dimethylethylenediamine trimethylamine, methyldiethanolamine, dimethylethanolamine N,N-diethanol,N',N'dimethylethylenediamine, N,N,N'triethanol-N-methylethylenediamine recovered therefrom.

EXAMPLE 10

The following examples illustrate other modes of practice presently contemplated with one or more tertiary amine and tertiary diamine species:

In a quartz-lined Parr general purpose bomb reactor are added 5 grams of tetraethylethylenediamine, 20 mmoles of (trimethylsilylethyl)diethylamine, 5 ml of isopropyl alcohol, 0.5 mmol in 1:1 ratio of $Rh_6(CO)_{16}/Fe_3(CO)_{16}(CO)_{12}$ catalyst under 100 lb in$^{-2}$ $N_2$ at 150° C. for 10 hours. The contents are removed and the products N,N-trimethylsilylethyl,N'N'diethylethylenediamine and triethylamine recovered therefrom.

In a quartz-lined Parr general purose bomb reactor are added 5 grams of tetra-n-propylethylenediamine, 20 mmoles of triethylamine, 5 ml of cyclohexyl alcohol, 0.5 mmol in 1:1 ratio of $Rh_6(CO)_{16}/Fe_3(CO)_{12}$ catalyst under 100 lb in$^{-2}$ CO at 150° C. for 10 hours. The contents are removed and the products diethylpropylamine, dipropylethylamine, tripropylamine, ethyl,tripropyl-ethylenediamine, N,N-diethyl,N'N'dipropylethylenediamine, N'N'dipropyl,N,N'diethylethylenediamine, triethylpropylethylenediamine, tetraethylethylenediamine recovered therefrom.

Since certain changes in carrying out the above process which embody the invention may be made without departing from its scope, it is intended that all matter contained in the above description shall be interpreted as illustrative and not in a limiting sense.

Having fully disclosed our invention, and provided teachings which will enable others to use our invention, the scope of our claims may now be understood as follows:

What is claimed is:

1. In the catalytic exchange of organic groups, involving the breaking of Z—N bonds, between one or more molecular species wherein $R^1$ and $R^2$ are the same or different monovalent organic groups bonded to the adjacent nitrogen atom by Z—N bonds, Z is a Group IV$_a$ atom, n is zero or a positive integer, $R^3$ is an organic group bonded to the adjacent nitrogen atom or atoms by Z—N bonds and is monovalent where n is zero and polyvalent where n is a positive integer, $R^4$ and $R^5$ are the same or different monovalent organic groups bonded to the adjacent nitrogen atom or atoms by Z—N bonds or together form a bivalent organic group bonded to the adjacent nitrogen atom or atoms by Z—N bonds, the improvement consisting essentially of conducting such catalytic exchange reaction under conditions substantially free of water and employing a homogeneous catalyst in the presence of an alcohol solvent and carbon monoxide, said catalyst being a Group VIII metal or mixed-metal complex or salt of said catalyst.

2. The improvement of claim 1 wherein said Group VIII metal or mixed-metal complex is a complex selected from the group consisting of a complex of cobalt, rhodium, iridium, iron, ruthenium, osmium, or mixtures thereof.

3. The improvement of claim 1 wherein Z is carbon.

4. The improvement of claim 1 wherein said Group VIII metal or mixed-metal complex is a complex selected from the group consisting of a complex of rhodium, iridium, iron, ruthenium, osmium, or mixtures thereof.

5. The improvement of claim 1 wherein said Group VIII metal or mixed-metal complex is a complex selected from the group consisting of a complex of rhodium, iridium, iron, ruthenium, osmium, or mixtures thereof.

6. The improvement of claim 1 wherein said Group VIII metal complex is a metal carbonyl or metalcarbonyl hydride.

7. The improvement of claim 1 wherein said Group VIII metal complex is a metal carbonyl.

8. The improvement of claim 3 wherein said Group VIII mixed-metal complex is a complex selected from iron-ruthenium or iron-osmium.

9. The improvement of claim 3 wherein said Group VIII mixed-metal complex is iron-ruthenium.

10. The improvement of claim 6 wherein said Group VIII metal complex is a trimetalododecacarbonyl or dihydridodecacarbonyl having the general formula $$H_2M_3(CO)_{10}$$

wherein M is said Group VIII metal.

11. The improvement of claim 1 wherein said alcohol solvent is methanol or ethanol.

12. The improvement of claim 7 wherein said Group VIII metal complex is a trimetalododecacarbonyl or dihydridodecacarbonyl having the general formula $$M_3(CO)_{12}$$

wherein M is said Group VIII metal.

13. The improvement of claim 11 wherein said Group VIII metal complex is a metal carbonyl.

14. The improvement of claims 1, 4, 8, 9 or 11 wherein the reacting species is a single diamine and $n = 1$.

15. The improvement of claim 14 wherein the reaction results in a polymeric mixture having the repeating mer unit $$\left[ -R^3 - \underset{\underset{R^1}{|}}{N} - \right].$$

16. The improvement of claims 1, 8, 9 or 11 wherein the reacting species are a mixture of two or more tertiary amines having the general formula $$\begin{array}{c} R^1 \\ \phantom{R^1}\diagdown \\ \phantom{R^1}\phantom{\diagdown}N-R^3 \\ \phantom{R^1}\diagup \\ R^2 \end{array}$$

and wherein $R^1$, $R^2$, and $R^3$ collectively differ among the species.

17. In an improved process for the production of mixed tertiary amines by the catalytic exchange of organic groups between a one, two or more component mixture of tertiary amines having the general formula, (ii) $[-(CH_2)_xNR_2]_kNR_{3-k}$, in combination with one or more tertiary amines having the same or different general formulae, (iii) $R_3N$, (iv) $(ZR_3)_jNR_{3-j}$, (v) $[-(CH_2)_xNZR_3]_kNR_{3-k}$, (vi) $NH_2(CH_2)_xNR_2$, (vii) $RNH(CH_2)_xNR_2$, wherein x is from 1 to about 18 carbon atoms; wherein j is 1 to 2; wherein k is 1, 2, or 3; wherein R is the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; wherein $R^6$ is hydrogen or the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; wherein Z is carbon, the improvement consisting essentially of conducting such catalytic exchange reaction under conditions substantially free of water and employing a homogeneous catalyst in the presence of an alcohol solvent and carbon monoxide, said catalyst being a Group VIII metal or mixed-metal complex or salt, said metal or mixed-metal is selected from the group consisting of a complex of cobalt, rhodium, iridium, iron, ruthenium, osmium, or mixtures thereof.

18. In an improved process for the production of mixed tertiary amines by the catalytic exchange of organic groups between a one, two or more component mixture of tertiary amines having the general formula, (iii) $R_3N$;

(iv) $(ZR_3)_jNR_{3-j}$;

wherein j is 1 to 2; wherein R is the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; wherein Z is carbon, the improvement consisting essentially of conducting such catalytic exchange reaction under conditions substantially free of water and employing a homogeneous catalyst in the presence of an alcohol solvent and carbon monoxide, said catalyst being a Group VIII metal or mixed-metal complex or salt, wherein said metal or mixed-metal complex is selected from the group consisting of a complex of cobalt, rhodium, iridium, iron, ruthenium, osmium, or mixtures thereof.

19. A process for the catalytic exchange of organic groups, involving the breaking of Z—N bonds, between one or more molecular species (i) wherein $R^1$ and $R^2$ are the same or different monovalent organic groups bonded to the adjacent nitrogen atom by Z—N bonds, Z is a Group $IV_a$ atom, n is zero or a positive integer, $R^3$ is an organic group bonded to the adjacent nitrogen atom or atoms by Z—N bonds and is monovalent where n is zero and polyvalent where n is a positive integer, $R^4$ and $R^5$ are the same or different monovalent organic groups bonded to the adjacent nitrogen atom or atoms by Z—N bonds or together form a bivalent organic group bonded to the adjacent nitrogen atom or atoms by Z—N bonds, the improvement consisting essentially of conducting such catalytic exchange reaction under conditions substantially free of water and employing a homogeneous catalyst in the presence of an alcohol solvent and carbon monoxide, said catalyst being a Group VIII mixed-metal complex or salt of said catalyst.

20. The improvement of claim 19 wherein said Group VIII mixed-metal complex is a complex selected from the group consisting of a complex of cobalt, rhodium, iridium, ruthenium, or osmium in admixture with iron.

21. The improvement of claim 19 wherein said Group VIII mixed-metal complex is a complex selected from the group consisting of a complex of rhodium, iridium, ruthenium, or osmium in admixture with iron.

22. The improvement of claim 19 wherein said Group VIII mixed-metal complex is a complex selected from the group consisting of a complex of rhodium, iridium, ruthenium, or osmium in admixture with iron.

23. In an improved process for the production of mixed tertiary amines by the catalytic exchange of organic groups between a one, two or more component mixture of tertiary amines having the general formula, (ii) $[-(CH_2)_xNR_2]_kNR_{3-k}$, in combination with one or more tertiary amines having the same or different general formulae, (iii) $R_3N$, (iv) $(ZR_3)_jNR_{3-j}$, (v) $[-(CH_2)_xNZR_3]_kNR_{3-k}$, (vi) $NH_2(CH_2)_xNR_2$, (vii) $RNH(CH_2)_xNR_2$, wherein x is from 1 to about 18 carbon atoms; wherein j is 1 to 2; wherein k is 1, 2, or 3; wherein R is the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; wherein $R^6$ is hydrogen or the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; wherein Z is carbon, the improvement consisting essentially of conducting such catalytic exchange reaction under conditions substantially free of water and employing a homogeneous catalyst in the presence of an alcohol solvent and carbon monoxide, said catalyst being a Group VIII mixed-metal complex or salt, said mixed-metal is selected from the group consisting of a complex of cobalt, rhodium, iridium, ruthenium, or osmium in admixture with iron.

24. In an improved process for the production of mixed tertiary amines by the catalytic exchange of organic groups between a one, two or more component mixture of tertiary amines having the general formula, (iii) $R_3N$;

(iv) $(ZR_3)_jNR_{3-j}$;

wherein j is 1 to 2; wherein R is the same or different organic group selected from a $C_{1-20}$ alkyl, a $C_{4-20}$ cycloalkyl, a $C_{6-12}$ aryl, a $C_{7-12}$ alkaryl, and a $C_{7-12}$ aralkyl; wherein Z is carbon, the improvement consisting essentially of conducting such catalytic exchange reaction under conditions substantially free of water and employing a homogeneous catalyst in the presence of an alcohol solvent and carbon monoxide, said catalyst being a Group VIII mixed-metal complex or salt, wherein said mixed-metal complex is selected from the group consisting of a complex of cobalt, rhodium, iridium, ruthenium, or osmium in admixture with iron.

* * * * *